United States Patent [19]

Futaki et al.

[11] Patent Number: 5,536,155

[45] Date of Patent: Jul. 16, 1996

[54] PRESERVATIVE OF CUT FLOWERS

[75] Inventors: Kouji Futaki, Tokyo; Keiko Shigeno, Chiba-ken; Keiko Hoshi, Tokyo, all of Japan

[73] Assignee: Asahi Kogaku Kogyo Kabushiki Kaisha, Tokyo, Japan

[21] Appl. No.: 281,076

[22] Filed: Jul. 27, 1994

[30] Foreign Application Priority Data

Jul. 27, 1993 [JP] Japan .................................. 5-184673

[51] Int. Cl.$^6$ .......................... A01N 65/00; A01N 59/00; A01N 59/08
[52] U.S. Cl. ...................... 424/195.1; 424/600; 424/678; 424/679; 514/25; 514/78; 514/557
[58] Field of Search ............................... 424/195.1, 600, 424/678, 679; 514/25, 78, 557

[56] References Cited

U.S. PATENT DOCUMENTS 4,423,030 12/1983 Hayes et al. ............................. 424/58

OTHER PUBLICATIONS

Potter's Cyclopedia, 1950, pp. 131–133.

*Primary Examiner*—John W. Rollins
*Attorney, Agent, or Firm*—Greenblum & Bernstein

[57] ABSTRACT

Preservatives for cut flowers which include an extract from eucalyptus leaves as a bactericidal agent. The preservative further includes at least one additive selected from naturally occurring bactericidal substances not found in the extract from eucalyptus leaves, saccharides, disinfectants, water-soluble mineral substances, calcium phosphate compounds, surface active substances and plant hormones. The preservative is effective to keep cut flowers fresh for an extended period of time, does not harmfully effect the flowers, and is safe and has no toxic effect to young children, when it is drunk by mistake.

38 Claims, No Drawings

PRESERVATIVE OF CUT FLOWERS

BACKGROUND OF THE INVENTION

1. Field of the Invention

The present invention relates to a preservative for cut flowers. More particularly, the present invention relates to a preservative or "activation agent" for maintaining cut flowers in a fresh state for an extended period of time.

2. Description of the Prior Art

Hitherto, many types of activation treatments have been adopted in order to keep cut flowers in a fresh state. For example, the conventional treatment methods for cut flowers in the house includes stem cutting under water, hot water treatment, charring of stem ends, stem crushing and the like. All of these methods are considered to be effective in attaining an increased level of water uptake of cut flowers, however, it is difficult to obtain a satisfactory level of water uptake. In fact, some of them will show only a little improvement of water uptake, if applied to specific cut flowers.

Further, it has been suggested that bactericides such as alum, vinegar, bleaching agent and the like should be added to the water. The use of bactericides in the water is intended to prevent rotting of the cut flowers and thereby keep the flowers fresh. However, the effects obtained by using such chemicals are not constant and good, and also may be vary depending upon the particular type of flower and other factors. In addition, since the conventional agents used in the preservative contain a synthetic substance as a principal component thereof, there is another problem that the synthetic substance causes harm to the flowers.

Japanese Unexamined Patent Publication (Kokai) No.4-120001 discloses a preservative of cut flowers which contains an anti-microbial metal such as a silver-loaded calcium phosphate compound. However, the anti-microbial metal has a toxic effect on the plant cells of the flowers, and also can cause a toxic reaction when consumed by persons, especially young children.

Under these circumstances, it is desired to develop a preservative for cut flowers which enables cut flowers to be kept in a fresh state for an extended period of time, contains none or if contained, the lowest amount possible, of synthetic chemical reagents, and is safe to the health of young children, if they should happen to consume the preservative.

SUMMARY OF THE INVENTION

The object of the present invention is to provide a cut flower preservative which is effective at keeping cut flowers fresh for an extended period of time, does not harmfully effect the flowers due to the chemical reagents contained therein, and is safe and has no toxicity to young children, when it is drunk by mistake.

According to the present invention, the above object can be attained by a preservative of cut flowers which comprises an extract from eucalyptus leaves, which is used as a bactericide.

The present disclosure relates to subject matter contained in Japanese patent application No.5-184673(filed on Jul. 27, 1993) which is expressly incorporated herein by reference in its entirety.

DESCRIPTION OF THE PREFERRED EMBODIMENTS

As described in the above paragraph, the cut flower preservative according to the present invention comprises an extract from eucalyptus leaves used as a bactericide.

The preservative is preferably provided as a concentrate. Prior to use thereof, the concentrated preservative may be diluted with a suitable amount of water such as city water or other diluent. Alternatively it may be added in drops to the water which the cut flowers are put in.

The extract from eucalyptus leaves may be prepared by subjecting the eucalyptus leaves to a conventional extraction process, or may be one of those commercially available. The maximum concentration of the extract is about 3% by weight of the water used for the cut flowers. The preferable concentration range of the extract is about 0.05 to 1% by weight of the water used for the cut flowers. Note that a concentration of the extract above about 3% by weight should be avoided, because although it can exhibit a detrimental bactericidal effect at these levels it can not provide a satisfactory preservative effect.

In addition to said extract from eucalyptus leaves, the cut flower preservative according to the present invention may comprise at least one additive selected from the group consisting of naturally occurring bactericidal substances not found in said extract of eucalyptus leaves, saccharides, disinfectants, water-soluble mineral substances, calcium phosphate compounds, surface active substances and plant hormones.

The preservative of the present invention may contain one or more of the naturally occurring bactericidal substances, in addition to the extract from eucalyptus leaves. Preferably, the natural bactericidal substance is selected from chitosan, hinokitiol, tea catechin, flavonol, extract from grapefruit seed, and the like. The natural bactericidal substance, if added, is preferably added to the preservative in an amount of about 3% by weight or less in terms of the concentration of the total natural bactericidal substances including the extract from eucalyptus leaves in the water which the cut flowers are put in.

Further, the preservative of the present invention may contain one or more of the saccharides selected from the group consisting of sucrose, fructose, glucose and the like. The saccharide can act as a nutrient component for the flowers. If added, it is preferably used in the preservative in an amount of about 5% by weight or less in terms of the concentration of the saccharide in the water for the cut flowers.

Furthermore, the preservative of the present invention may contain one or more of the organic acids, disinfectant, selected from the group consisting of citric acid, succinic acid, malic acid, tartaric acid, lactic acid and the like for use as a disinfectant. The disinfectant, if added, is preferably used in an amount of about 2% by weight or less in terms of the concentration of the disinfectant in the water used for the cut flowers.

Furthermore, the preservative of the present invention may further contain one or more water-soluble mineral substances. The mineral substances used herein are those obtained by mixing and fermenting plant seeds such as seeds of peach, apricot, walnut and the like with egg shells, and then extracting the fermentation product. The function of the mineral substances has not been clearly explained, however, it is the main observation that they can act as a dispersing agent for finely dividing the population of water molecules.

The water-soluble mineral substance contains ionized calcium, ionized magnesium, ionized potassium, ionized sodium, ionized iron and other ionized metals. Generally speaking, a preferred composition of the water-soluble mineral substance contains about 2100 mg of calcium, about 68 mg of magnesium, about 130 mg of sodium, about 6 mg of potassium, about 0.5 mg of iron and the like per 100 g of the mineral substance. The water-soluble mineral substance, if added, is preferably used in the preservative in an amount of about 10% by weight or less in terms of the concentration of the mineral substance in the water used for the cut flowers.

The preservative of the present invention may further contain one or more of calcium phosphate compounds. Preferably, the calcium phosphate compounds used herein have a ratio of Ca/P between about 1.5 and 2.0, and are selected from the group consisting of tricalcium phosphate, tetracalcium phosphate, hydroxyapatite and the like. The phosphate in the calcium phosphate compounds may act as a source of nutrient for cut flowers, and accordingly it can effectively contribute to the growth of flowers. The calcium phosphate compound, if added, is preferably used in the preservative in an amount of about 0.5% by weight or less in terms of the concentration of the phosphate compound in water which is used to receive cut flowers.

The preservative of the present invention may further contain one or more surface active substances. Preferably, the surface active substances used herein are selected from the group consisting of phospholipids such as cephalin, lecithin, phosphatidic acid and the like, and glycolipids such as sophorolipid and the like. The surface active substances can increase the dispersability of other components contained in the preservative in water, and at the same time, can accelerate the taking up of water. The surface active substance, if added, is preferably used in the preservative in an amount of about 0.5% by weight or less in terms of the concentration of the surface active substance in the water used for the cut flowers.

Moreover, the preservative for the present invention may contain one or more plant hormones. Suitable plant hormones include, for example, auxin, cytokine, gibberellin, abscisic acid, ethylene, brassinolide and the like. The content of the plant hormones in the preservative may be optionally varied depending upon the particular hormone used and other factors. However, generally, if added, the plant hormone is preferably used in the preservative in an amount of about 0.02% by weight or less in terms of the concentration of the hormone in the water used for the cut flowers.

As can be seen from the above descriptions, the cult flower preservative according to the present invention contains an extract from eucalyptus leaves, acting as a bactericidal, as one essential component of the preservative and also may contain some of the other components, mentioned above, in combination with the extract. A plurality of combinations of the components which will result in satisfactory effects are forseen in the practice of the present invention.

Of particular note, the inventors have found that a cut flower preservative containing the extract from eucalyptus leaves, saccharides, water-soluble mineral substances and calcium phosphate compounds, or containing the extract from eucalyptus leaves, saccharides, disinfectants, water-soluble mineral substances and calcium phosphate compounds, can exhibit a highly improved life expectancy without suffering from toxicity problems due to the chemicals used in the preservatives. When both the water-soluble mineral substances and calcium phosphate compounds are used together in the preservative, it is contemplated that the mineral substances were previously mixed with the calcium phosphate compounds to prepare a uniform dispersion thereof which is then mixed with other components.

The cut flower preservatives according to the present invention can be prepared by simply mixing the components necessary to complete the intended preservative in accordance with conventional mixing technologies. If necessary, water and other solvents may be used in suitable proportions.

The present invention will be further described in detail with reference to the following working examples. Note, however, that the present invention is not restricted to these examples.

EXAMPLE 1

The cut flower preservative containing 40% by weight of sucrose, 4% by weight of citric acid and 8% by weight of eucalyptus leaves extract and 42% by weight of water was prepared. The preservative was then diluted 40 times by volume with city water to make an aqueous preservative solution. The resulting preservative solution contained 1.0% by weight of sucrose, 0.1% by weight of citric acid and 0.2% by weight of eucalyptus leaves extract.

Two cut tulips were left sitting in the preservative solution in a room at a temperature of 24° to 32° C. and at a humidity of 21 to 50%. After 2, 4 and 6 days, the weight of each tulip was measured as an indication of how the water uptake of the cut flowers changed with time.

For comparison, the above procedure was repeated by putting cut flowers into two other solutions: Tokyo city water having no additive and a commercially available preservative product (hereinafter, referred as "preservative A").

The results are summarized in the following Table 1. Note, each weight is an average of the weights of the two cut flowers, and the weight of the fresh flowers, and flowers as cut, is regarded as to be 100%.

TABLE 1

| solution for dipping flowers | weight of cut flowers (%) measured | | | |
|---|---|---|---|---|
| | as cut | 2 days | 4 days | 6 days |
| city water | 100 | 100 | 98 | 90 |
| preservative A | 100 | 103 | 107 | 90 |
| preservative (invention) | 100 | 105 | 112 | 103 |

EXAMPLE 2

Two aqueous solutions containing the cut flower preservative according to the present invention were prepared.

| Composition of Test Solution 1: | |
|---|---|
| citric acid | 0.1% by weight |
| liquified hydroxyapatite (solution of 0.02 g of hydroxyapatite powders in 10 g of water-soluble minerals) | 10% by weight |
| eucalyptus leaves extract (as a bactericidal agent) | 1% by weight |
| Composition of Test Solution 2: | |
| citric acid | 0.02% by weight |

-continued

| | |
|---|---|
| liquified hydroxyapatite (see, above) | 2% by weight |
| eucalyptus leaves extract (as an bactericidal agent) | 0.2% by weight |

For the comparison, another solution was used for the cut flowers: Tokyo city water having no additive was provided.

Cut flowers of Rijnveld freezia were left dipped in the test solution in a vase (one cut flower per vase) in a room at a temperature of 25° to 31° C. and at a humidity of 25 to 53%. After 2, 4 and 6 days, the weight of each freezia was measured as an indication of how the water uptake of the cut flowers changed with time.

The results are summarized in the following Table 2. Note, each weight is an average of the weights of three cut flowers in three separate vases. And the weight of the fresh flowers, Note flowers as cut, is regarded as to be 100%.

TABLE 2

| solution for | weight of cut flowers (%) measured | | | |
|---|---|---|---|---|
| dipping flower | as cut | 2 days | 4 days | 6 days |
| city water | 100 | 86 | 83 | 77 |
| test solution 1 | 100 | 88 | 83 | 79 |
| test solution 2 | 100 | 98 | 92 | 81 |

EXAMPLE 3

Four aqueous solutions containing the cut flower preservative according to the present invention were prepared.

| Composition of Test Solution 3: | |
|---|---|
| citric acid | 0.02% by weight |
| liquified hydroxyapatite (same as that of test solution 1) | 2.0% by weight |
| eucalyptus leaves extract (as a bactericidal agent) | 0.2% by weight |
| Composition of Test Solution 4: | |
| sucrose | 0.1% by weight |
| liquified hydroxyapatite (same as that of test solution 1) | 0.1% by weight |
| eucalyptus leaves extract (as a bactericidal agent) | 0.02% by weight |
| Composition of Test Solution 5: | |
| Sucrose | 1.0% by weight |
| citric acid | 0.1% by weight |
| liquified hydroxyapatite (same as that of test solution 1) | 0.1% by weight |
| eucalyptus leaves extract (as a bactericidal agent) | 0.2% by weight |
| Composition of Test Solution 6: | |
| Sucrose | 3.0% by weight |
| citric acid | 0.5% by weight |
| liquified hydroxyapatite (same as that of test solution 1) | 0.2% by weight |
| eucalyptus leaves extract (as a bactericidal agent) | 0.2% by weight |

For comparison, another solution was used for the cut flowers: Tokyo city water having no additive was provided.

Cut flowers of Arisetter' spray carnation were left dipped in the test solution in a vase (one cut flower per vase) in a room at a temperature of 23° to 25.5° C. and at a humidity of 41 to 58%. After 2, 4 and 6 days, the weight of each spray carnation was measured as an indication of how the water uptake of the cut flowers changed with time.

The results are summarized in the following Table 3. Note, each weight is an average of the weights of three cut flowers in three separate vases, and the weight of the fresh flowers, Note flowers as cut. Is regarded as to be 100%.

TABLE 3

| solution for | weight of cut flowers (%) measured | | | |
|---|---|---|---|---|
| dipping flower | as cut | 2 days | 4 days | 6 days |
| city water | 100 | 106 | 96 | 86 |
| test solution 3 | 100 | 105 | 96 | 92 |
| test solution 4 | 100 | 104 | 108 | 99 |
| test solution 5 | 100 | 106 | 111 | 108 |
| test solution 6 | 100 | 104 | 122 | 124 |

EXAMPLE 4

Three aqueous solutions containing the cut flower preservative according to the present invention were prepared, along with one control solution.

| Composition of Test Solution 7: | |
|---|---|
| cane sugar | 3.0% by weight |
| citric acid | 0.5% by weight |
| eucalyptus leaves extract (as a bactericidal agent) | 0.2% by weight |
| Composition of Test Solution 8: | |
| sucrose | 3.0% by weight |
| citric acid | 0.5% by weight |
| liquified hydroxyapatite (same as that of test solution 1) | 0.2% by weight |
| eucalyptus leaves extract (as an bactericidal agent) | 0.2% by weight |
| Composition of Test Solution 9 (control): | |
| sucrose | 3.0% by weight |
| citric acid | 0.5% by weight |
| Composition of Test Solution 10: | |
| sucrose | 3.0% by weight |
| citric acid | 0.5% by weight |
| hydroxyapatite powders | 0.04% by weight |
| eucalyptus leaves extract (as a bactericidal agent) | 0.2% by weight |

Cut flowers of Rote Rose, rose were left dipped in the test solution in a vase (one cut flower per vase) in a room at a temperature of 23° to 26° C. and at a humidity of 61 to 74%. After 1, 2, 5 and 6 days, the weight of each rose was measured as an indication of how the water uptake of the cut flowers changed with time.

The results are summarized in the following Table 4. Note, each weight is an average of the weights of two cut flowers in two separate vases, and the weight of the fresh flowers, Note flowers as cut. Is regarded as to be 100%.

TABLE 4

| solution for | weight of cut flowers (%) measured | | | | |
|---|---|---|---|---|---|
| dipping flower | as cut | 1 day | 2 days | 5 days | 6 days |
| test solution 7 | 100 | 102 | 107 | 99 | 88 |
| test solution 8 | 100 | 102 | 106 | 105 | 96 |
| test solution 9 | 100 | 100 | 103 | 76 | 61 |
| test solution 10 | 100 | 102 | 107 | 91 | 78 |

The above-described examples indicate that the cut flower preservatives of the present invention are able to keep cut flowers fresh, for an extended period of time, exhibit an excellent increased life expectancy, have no harmful effect on the flowers, and are also safe since they have no toxic effect to persons, for example, young children, when they are mistakenly consumed.

What is claimed is:

1. A preservative of cut flowers, comprising:
   an extract from eucalyptus leaves used as a bactericidal agent; and
   at least one additive selected from the group consisting of chitosan, hinokitiol, tea catechin, flavonol, extract from grapefruit seed, hydroxyapatite, phospholipids, glycolipids and plant hormones;
   wherein said extract from eucalyptus leaves is contained in an amount of about 3% by weight or less in terms of the concentration of said extract from eucalyptus leaves in a volume of water which the cut flowers are put in.

2. A preservative of cut flowers according to claim 1, further comprising:
   at least one additive selected from the group consisting of saccharides, disinfectants and water-soluble mineral substances.

3. A preservative of cut flowers according to claim 1, wherein said saccharides include at least one member selected from the group consisting of sucrose, fructose and glucose.

4. A preservative of cut flowers according to claim 3 wherein said saccharides are used in the preservative in an amount of about 5% by weight or less in terms of the concentration of the saccharide in the water which the cut flowers are put in.

5. A preservative of cut flowers according to claim 1, wherein said disinfectants include at least one organic acid selected from the group consisting of citric acid, succinic acid, malic acid, tartaric acid and lactic acid.

6. A preservative of cut flowers according to claim 5, wherein said disinfectants are used in the preservative in an amount of about 2% by weight or less in terms of the concentration of the disinfectants in the water which the cut flowers are put in.

7. A preservative of cut flowers according to claim 2, wherein said water soluble mineral substance includes at least one ionized metal selected from the group consisting of calcium, magnesium, potassium, sodium and iron.

8. A preservative of cut flowers according to claim 7, wherein said water-soluble mineral substances are used in the preservative in an amount of about 10% by weight or less in terms of the concentration of said mineral substances in water for putting cut flowers.

9. A preservative of cut flowers according to claim 1, wherein said at least one additive is added to the preservative in an amount of about 3% by weight or less in terms of the concentration of the total natural bactericidal substance including said extract from eucalyptus leaves in the water which the cut flowers are put in.

10. A preservative of cut flowers according to claim 1, wherein said plant hormones include a member selected from the group consisting of auxin, cytokine, gibberellin, abscisic acid, ethylene and brassinolide.

11. A preservative of cut flowers according to claim 10, wherein said plant hormones are used in the preservative in an amount of about 0.02% by weight or less in terms of the concentration of the hormones in the water which the cut flowers are put in.

12. A preservative of cut flowers according to claim 1, wherein said hydroxyapatite is used in the preservative in an amount of about 0.5% by weight or less in terms of the concentration of the hydroxyapatite in the water which the cut flowers are put in.

13. A preservative of cut flowers according to claim 1, wherein said phospholipids are used in the preservative in an amount of about 0.5% by weight or less in terms of the concentration of said phospholipids in the water in which the cut flowers are placed.

14. A preservative of cut flowers according to claim 1, further comprising at least one additive from the group consisting of:
   water-soluble mineral substances; saccharides and calcium phosphate compounds.

15. A preservative of cut flowers according to claim 1, further comprising at least one additive from the group consisting of:
   water-soluble mineral substances; saccharides, disinfectants and calcium phosphate compounds.

16. A preservative of cut flowers according to claim 1, wherein said glycolipids are used in the preservative in an amount of about 0.5% by weight or less in terms of the concentration of said glycolipids in the water in which the cut flowers are placed.

17. A preservative of cut flowers according to claim 1, wherein said hydroxyapatite is liquified hydroxyapatite.

18. A preservative of cut flowers, comprising:
   an extract of eucalyptus leaves used as a bactericidal agent; and
   at least one additive selected from the group consisting of chitosan, hinokitiol, tea catechin, flavonol, extract from grapefruit seed, ionized calcium, ionized magnesium, ionized iron, phospholipids, glycolipids, calcium phosphate compounds in an amount of about 0.5% by weight or less in terms of the concentration of phosphate compound in the water in which the cut flowers are placed, and plant hormones;
   wherein said extract from eucalyptus leaves is contained in an amount of about 3% by weight or less in terms of the concentration of said extract from eucalyptus leaves in a volume of water which the cut flowers are put in.

19. A method of preserving cut flowers, comprising:
   preparing a preservative comprising an extract of eucalyptus leaves used as a bactericidal agent; and
   contacting the cut stems of cut flowers with the preservative;
   wherein said extract from eucalyptus leaves is contained in the preservative in an amount of about 3% by weight or less.

20. A method of preserving cut flowers according to claim 19, wherein preparing a preservative comprises preparing a solution comprising an extract of eucalyptus leaves.

21. A method of preserving cut flowers according to claim 20, wherein the solution prepared is an aqueous solution.

22. A method of preserving cut flowers according to claim 19, wherein preparing a preservative further comprises:
   adding to the preservative at least one additive selected from the group consisting of naturally occurring bactericidal substances not found in said extract of eucalyptus leaves, saccharides, disinfectants, water-soluble mineral substances, calcium phosphate compounds, surface active substances and plant hormones.

23. A method of preserving cut flowers according to claim 22, wherein the naturally occurring bactericidal substances are selected from the group consisting of chitosan, hinokitiol, tea catechin, flavonol, extract from grapefruit seed and combinations thereof.

24. A method of preserving cut flowers according to claim 23, wherein the preservative is an aqueous solution and the naturally occurring bactericidal substances are added to the aqueous solution in an amount of about 3% by weight or less of the total weight of the aqueous solution.

25. A method of preserving cut flowers according to claim 22, wherein the saccharides are selected from the group consisting of sucrose, fructose, glucose and combinations thereof.

26. A method of preserving cut flowers according to claim 25, wherein the preservative is an aqueous solution and the saccharides are added to the aqueous solution in an amount of about 5% by weight or less of the total weight of the aqueous solution.

27. A method of preserving cut flowers according to claim 22, wherein the disinfectants are selected from the group of organic acids consisting of citric acid, succinic acid, malic acid, tartaric acid, lactic acid and combinations thereof.

28. A method of preserving cut flowers according to claim 27, wherein the preservative is an aqueous solution and the disinfectants are added to the aqueous solution in an amount of about 2% by weight or less of the total weight of the aqueous solution.

29. A method of preserving cut flowers according to claim 22, wherein the water soluble mineral substances are selected from the group consisting of ionized calcium, ionized magnesium, ionized potassium, ionized sodium, ionized iron and combinations thereof.

30. A method of preserving cut flowers according to claim 29, wherein the preservative is an aqueous solution and the water soluble mineral substances are added to the aqueous solution in an amount of about 10% by weight or less of the total weight of the aqueous solution.

31. A method of preserving cut flowers according to claim 22, wherein the calcium phosphate compounds have a Ca/P ratio of between about 1.5/1 and 2.0/1 and are selected from the group consisting of tricalcium phosphate, tetracalcium phosphate, hydroxyapatite and combinations thereof.

32. A method of preserving cut flowers according to claim 31, wherein the preservative is an aqueous solution and the calcium phosphate compounds are added to the aqueous solution in an amount of about 0.5% by weight or less of the total weight of the aqueous solution.

33. A method of preserving cut flowers according to claim 22, wherein the surface active substances are selected from the group consisting of phospholipids, glycolipids and combinations thereof.

34. A method of preserving cut flowers according to claim 33, wherein the preservative is an aqueous solution and the surface active substances are added to the aqueous solution in an amount of about 0.5% by weight or less of the total weight of the aqueous solution.

35. A method of preserving cut flowers according to claim 22, wherein the plant hormones are selected from the group consisting of auxin, cytokine, gibberellin, abscisic acid, ethylene, brassinolide and combinations thereof.

36. A method of preserving cut flowers according to claim 35, wherein the preservative is an aqueous solution and the plant hormones are added to the aqueous solution in an amount of about 0.02% by weight or less of the total weight of the aqueous solution.

37. A method of preserving cut flowers according to claim 19, wherein preparing a preservative further comprises:
    preparing an aqueous solution comprising an extract of eucalyptus leaves, at least one saccharide, at least one water-soluble mineral substance and at least one calcium phosphate containing compound.

38. A method of preserving cut flowers according to claim 19 wherein preparing a preservative further comprises:
    preparing an aqueous solution comprising an extract of eucalyptus leaves, at least one saccharide, at least one disinfectant, at least one water-soluble mineral substance and at least one calcium phosphate containing compound.

* * * * *

UNITED STATES PATENT AND TRADEMARK OFFICE
CERTIFICATE OF CORRECTION

PATENT NO. : 5,536,155
DATED : July 16, 1996
INVENTOR(S) : K. FUTAKI et al.

It is certified that error appears in the above-indentified patent and that said Letters Patent is hereby corrected as shown below:

On the cover, in section [56], "References Cited", "U.S. PATENT DOCUMENTS", line 2, insert ---5,009,898 4/1991 Sakuma et al. 424/618---.

On the cover, in section [56], "References Cited", "U.S. PATENT DOCUMENTS", line 1, insert ---5,268,174 12/1993 Sakuma et al. 424/195.1---.

On the cover, in section [56], "References Cited", under the heading "FOREIGN PATENT DOCUMENTS", insert --- 4120001 4/1992 Japan---.

At column 7, line 22 (claim 3, line 1), change "1," to ---2,---.

At column 7, line 30 (claim 5, line 1), change "1," to ---2,---.

Signed and Sealed this

Twenty-first Day of January, 1997

Attest:

BRUCE LEHMAN

*Attesting Officer*  *Commissioner of Patents and Trademarks*